United States Patent
Pingel et al.

(10) Patent No.: US 6,903,069 B2
(45) Date of Patent: Jun. 7, 2005

(54) FACTOR VII GLYCOFORMS

(75) Inventors: Hans Kurt Pingel, Farum (DK); Niels Kristian Klausen, Gentofte (DK)

(73) Assignee: Novo Nordisk Health Care A/S, Zurich (CH)

(*) Notice: Subject to any disclaimer, the term of this patent is extended or adjusted under 35 U.S.C. 154(b) by 136 days.

(21) Appl. No.: 09/969,357

(22) Filed: Oct. 2, 2001

(65) Prior Publication Data

US 2002/0137673 A1 Sep. 26, 2002

Related U.S. Application Data

(60) Provisional application No. 60/276,322, filed on Mar. 16, 2001, provisional application No. 60/271,581, filed on Feb. 26, 2001, and provisional application No. 60/238,944, filed on Oct. 10, 2000.

(30) Foreign Application Priority Data

| Oct. 2, 2000 | (DK) | 2000 01456 |
| Feb. 16, 2001 | (DK) | 2001 00262 |
| Mar. 14, 2001 | (DK) | 2001 00430 |
| May 14, 2001 | (DK) | 2001 00751 |

(51) Int. Cl.[7] .......... A61K 35/14; A61K 38/00; C07K 14/00; C12N 15/00
(52) U.S. Cl. .......... 514/2; 530/384; 435/69.1; 435/69.6; 435/254.1; 435/325; 435/183; 435/348; 435/358; 514/802; 514/834
(58) Field of Search .......... 530/384; 435/69.1, 435/69.6, 254.1, 325, 183, 348, 358; 514/2, 802, 834

(56) References Cited

U.S. PATENT DOCUMENTS

| 4,783,940 A | 11/1988 | Sato et al. ............ 52/223 |
| 4,784,950 A | * 11/1988 | Hagen et al. |
| 5,580,560 A | 12/1996 | Nicolaisen et al. ...... 424/94.64 |
| 6,100,061 A | 8/2000 | Reiter et al. ............ 435/69.1 |

FOREIGN PATENT DOCUMENTS

| WO | WO 01/11021 A1 | 8/1999 |
| WO | WO 00/28065 | 5/2000 |

OTHER PUBLICATIONS

Varkii, Ajit. (2001) Biochimie vol. 83, pp. 615–622.*
Baker et al. (May 5, 2001) BioTechnology and BioEngineering, vol. 73, No. 3, pp. 188–202.*
Tangvoranuntakul et al. (Oct. 14, 2003) Proc. Natl. Acad. Sci. vol. 100, No. 21, pp. 12045–12050.*
Raju et al. (2000) Glycobiology, vol. 10, No. 55, pp. 477–486.*
Jenkins, N. amd Curling, E.M.A. Glycosylation of recombinant proteins: Problems and Prospects. May 1994, Enzyme Microb. Technol. vol. 16, pp. 354–364.*
Nakagaki et al. Initiation of the Extrinsic Pathway of Blood Coagulation: Evidence for the Tissue Factor Dependent Autoactivation of Human Coagulation Factor VII. Nov. 1991 Biochemistry, vol. 30, No. 45, pp. 10819–10824.*
Bragonzi et al., Biochimica et Biophysica Acta, vol. 1474, pp. 273–282 (2000).
Bjoern et al., The Journal of Biological Chemistry, vol. 266, No. 17, pp. 11051–11057 (1991).
Broad et al., Cytotechnology, vol. 5, pp. 47–55 (1991).
Gawlitzek et al., Journal of Biotechnology, vol. 42, pp. 117–131 (1995).
Grabenhorst et al., Glycoconjugate Journal, vol. 16, pp. 81–97 (1999).
Jurlander et al., Seminars in Thrombosis and Hemostasis, vol. 27, No. 4, pp. 373–383 (2001).
Kemball–Cook et al., Gene, vol. 139, pp. 275–279 (1994).
Klausen et al., Molecular Biotechnology, vol. 9, pp. 195–204 (1998).
Klausen et al., Journal of Chromatography A, vol. 718, pp. 195–202 (1995).
Roddie et al., Blood Reviews, vol. 11, pp. 169–177 (1997).
Thim et al., Biochemistry, vol. 27, No. 20, pp. 7785–7793 (1988).
Weber et al., Analytical Biochemistry, vol. 225, pp. 135–142 (1995).
Weikert et al., Nature Biotechnology, vol. 17, pp. 1116–1121 (1999).

* cited by examiner

*Primary Examiner*—Jon Weber
*Assistant Examiner*—Holly Schnizer
(74) *Attorney, Agent, or Firm*—Reza Green; Lan S. Smith; Richard Bork

(57) ABSTRACT

The present invention provides preparations of Factor VIIa polypeptides or Factor VIIa-related polypeptides that exhibit predetermined glycoform patterns. The preparations of the invention exhibit improved functional properties and are useful for treating Factor VII-mediated conditions.

27 Claims, No Drawings

FACTOR VII GLYCOFORMS

CROSS REFERENCE TO RELATED APPLICATIONS

This application claims priority under 35 U.S.C. 119 of Danish application no. PA 2000 01456 filed on Oct. 2, 2000; PA 2001 00262 filed Feb. 16, 2001; PA 2001 00430 filed Mar. 14, 2001; and PA 2001 00751 filed on May 14, 2001 and U.S provisional applications Nos. 60/238,944 filed on Oct. 10, 2000; 60/271,581 filed on Feb. 26, 2001; and 60/276,322 filed on Mar. 16, 2001, the contents of which are fully incorporated herein by reference.

FIELD OF THE INVENTION

The present invention relates to compositions comprising Factor VII and other blood clotting factors having altered patterns of asparagine-linked glycosylation.

BACKGROUND OF THE INVENTION

The proteins involved in the clotting cascade, including, e.g., Factor VII, Factor VIII, Factor IX, Factor X, and Protein C, are proving to be useful therapeutic agents to treat a variety of pathological conditions. Accordingly, there is an increasing need for formulations comprising these proteins that are pharmaceutically acceptable and exhibit a uniform and predetermined clinical efficacy.

Because of the many disadvantages of using human plasma as a source of pharmaceutical products, it is preferred to produce these proteins in recombinant systems. The clotting proteins, however, are subject to a variety of co- and post-translational modifications, including, e.g., asparagine-linked (N-linked) glycosylation; O-linked glycosylation; and γ-carboxylation of glu residues. These modifications may be qualitatively or quantitatively different when heterologous cells are used as hosts for large-scale production of the proteins. In particular, production in heterologous cells often results in a different array of glycoforms, which are identical polypeptides having different covalently linked oligosaccharide structures.

In different systems, variations in the oligosaccharide structure of therapeutic proteins have been linked to, inter alia, changes in immunogenicity and in vivo clearance. Thus, there is a need in the art for compositions and methods that provide clotting protein preparations, particularly preparations comprising recombinant human Factor VII, modified Factor VII, or Factor VII-related polypeptides, that contain predetermined glycoform patterns.

SUMMARY OF THE INVENTION

The present invention relates to preparations comprising Factor VII polypeptides or Factor VII-related polypeptides that exhibit predetermined glycoform patterns. As used herein, a Factor VII or Factor VII-related preparation refers to a plurality of Factor VII or Factor VII-related polypeptides, including variants and chemically modified forms, as well as forms that have been proteolytically activated (e.g., Factor VIIa), that have been separated from the cell in which they were synthesized. A glycoform pattern refers to the distribution within the preparation of oligosaccharide chains having varying structures that are covalently linked to Factor VII polypeptides or Factor VII-related polypeptides.

In one aspect, the invention provides a preparation comprising a plurality of Factor VII polypeptides or Factor VII-related polypeptides, wherein the polypeptides comprise asparagine-linked oligosaccharide chains and wherein one or more of the following applies: (i) between about 94–100% of the oligosaccharide chains comprise at least one sialic acid moiety; (ii) between about 0–7% of the oligosaccharide chains have a neutral charge; (iii) less than about 16%, such as, e.g., between about 6–16% of the oligosaccharide chains comprise at least one terminal galactose residue; (iv) less than about 25%, such as, e.g., between about 6–9% of the oligosaccharide chains comprise at least one terminal N-acetylgalactosamine residue; or (v) less than about 30%, such as, e.g., between about 11–23% of the oligosaccharide chains comprise at least one terminal galactose or N-acetylgalactosamine residue. In some embodiments, in addition to one or more of (i)–(v): all of the sialic acid residues in the oligosaccharide chains are linked to galactose via an α2→3 linkage; at least some of the sialic acid residues comprise N-glycolyineuraminic acid (Neu5Gc) in addition to N-acetylneuraminic acid (Neu5Ac); and/or the oligosaccharide chains comprise fucose residues linked α1→6 to a core N-acetylglucosamine. In one embodiment, the invention encompasses a preparation comprising wild-type Factor VIIa in which between about 94–100% of the oligosaccharide chains have at least one sialic acid residue and all of the sialic acid residues are linked to galactose via an α2→3 linkage. In another embodiment, the invention encompasses a preparation comprising wild-type Factor VIIa in which between about 94–100% of the oligosaccharide chains have at least one sialic acid residue and at least some of the sialic acid residues are N-glycolyineuraminic acid. In yet another embodiment, the invention encompasses a preparation comprising wild-type Factor VIIa in which between about 94–100% of the oligosaccharide chains have at least one sialic acid residue and at least some of the chains contain N-acetylgalactosamine. The preparations of the present invention thus do not encompass wild-type Factor VII or Factor VIIa that has been isolated from human plasma and has not been modified ex vivo by glycosidase treatment.

In another aspect, the invention provides a preparation comprising a plurality of Factor VII polypeptides or Factor VII-related polypeptides, wherein the polypeptides comprise asparagines-linked oligosaccharide chains and wherein at least about 2% of the oligosaccharide chains contain at least one fucose linked α1→3 to an antennary N-acetylglucosamine residue (i.e., an N-acetylglucosamine residue that is linked β1→2,4, or 6 to a Man residue). Preferably, at least about 5% of the oligosaccharide chains contain at least one such antennary fucose residue; more preferably, at least about 10% or 20%; and most preferably, at least about 40%.

The preparations according to invention may comprise one or more of unmodified wild-type Factor VII; wild-type Factor VII that has been subjected to chemical and/or enzymatic modification; and Factor VII variants having one or more alterations in amino acid sequence relative to wild-type Factor VII. The preparations of the invention may be derived from human cells expressing Factor VII from an endogenous Factor VII gene or from cells programmed to express Factor VII or a Factor VII-related polypeptide from a recombinant gene.

In another aspect, the invention provides preparations comprising Factor VII or Factor VII-related polypeptides that exhibit one or more improved functional properties, including, without limitation, increased storage stability, bioavailability, half-life, and/or tissue factor-independent thrombin generating activity. In one embodiment, a Factor VII preparation comprising asparagine-linked oligosaccharide chains in which at least about 2% of the oligosaccharide chains contain at least one fucose linked α1→3 to an antennary N-acetylglucosamine residue exhibits tissue factor-independent thrombin generating activity that is at least about 110% that of a reference preparation, preferably at least about 125% and most preferably at least about 140%, when the oligosaccharides of the reference preparation lack fucose linked α1→3 to an antennary N-acetylglucosamine.

In another aspect, the invention encompasses methods for determining and/or optimizing the glycoform pattern of Factor VII and Factor VII-related polypeptides, which are carried out by the steps of:

(a) culturing a cell expressing Factor VII or Factor VII-related polypeptides under a first set of predetermined culture conditions;

(b) recovering Factor VII or Factor VII-related polypeptides from the culture to obtain a preparation comprising the polypeptides; and (c) analyzing the structure of the oligosaccharides linked to the polypeptides to determine the glycoform pattern of the preparation.

The methods may further comprise altering the culture conditions of step (a) to achieve a second set of predetermined culture conditions; and repeating the steps until a desired glycoform pattern is achieved. Alternatively, the methods may further comprise treating the preparation chemically or enzymatically to alter the oligosaccharide structure; and repeating the steps until a desired glycoform pattern is achieved. Furthermore, the methods may comprise the additional steps of subjecting preparations having predetermined glycoform patterns to at least one test of bioactivity or other functionality (such as, e.g., pharmacokinetic profile or stability), and correlating particular glycoform patterns with particular bioactivity or functionality profiles.

In another aspect, the invention provides methods for producing a preparation comprising Factor VII polypeptides or Factor VII-related polypeptides having a predetermined pattern of N-linked glycosylation. In some embodiments, the methods are carried out by culturing a cell expressing the polypeptides under conditions in which at least about 94% of the asparagine-linked oligosaccharides linked to the Factor VII polypeptides or Factor VII-related polypeptides comprise at least one sialic acid residue, e.g., one, two, three, or four sialic acid residues. In some embodiments, the methods are carried out by culturing a cell expressing the polypeptides under conditions in which at least about 5% of the oligosaccharide chains contain at least one fucose linked α1→3 to an antennary N-acetylglucosamine residue. In some embodiments, Factor VII polypeptides or Factor VII-related polypeptides, irrespective of their source, are subjected to enzymatic treatments to achieve the desired glycoform patterns.

In another aspect, the invention provides pharmaceutical formulations comprising the preparations of the invention and methods of preventing and/or treating syndromes that are responsive to Factor VII polypeptides or Factor VII-related polypeptides. The methods comprise administering the pharmaceutical formulations to a patient in need of treatment, under conditions that result in either an enhancement or inhibition in blood clotting. In one series of embodiments, Factor VII preparations are administered when it is desired to enhance blood clotting, such as, e.g., in haemophilia A, haemophilia B, Factor XI deficiency, Factor VII deficiency, thrombocytopenia, or von Willebrand's disease; in syndromes accompanied by the presence of a clotting factor inhibitor; before, during, or after surgery or anticoagulant therapy; or after trauma. In another series of embodiments, preparations of Factor VII-related polypeptides (i.e., preparations having reduced or modified bioactivity relative to wild-type Factor VII) are administered to reduce blood clotting, such as, e.g., in patients undergoing angioplasty or those suffering from deep vein thrombosis, pulmonary embolism, stroke, disseminated intravascular coagulation (DIC), fibrin deposition in lungs and kidneys associated with gram-negative endotoxemia, or myocardial infarction. According to the invention, preparations of Factor VII-related polypeptides may also be administered when it is desired to modify, such as, e.g., reduce, intracellular signalling via a tissue factor (TF)-mediated pathway, to treat conditions such as, e.g., Acute Respiratory Distress Syndrome (ARDS), Systemic Inflammatory Response Syndrome (SIRS), Hemolytic Uremic Syndrome (HUS), Multiple Organ Failure (MOF), and thrombocytopenia purpura (TTP).

DETAILED DESCRIPTION OF THE INVENTION

The present inventors have discovered that preparations of coagulation proteins having predetermined glycoform patterns exhibit improved functional properties. Accordingly, the present invention relates to methods and compositions that provide these protein preparations. In particular, the invention relates to preparations comprising Factor VII polypeptides and Factor VII-related polypeptides having specific predetermined patterns of asparagine-linked (N-linked) oligosaccharides. The preparations of the invention exhibit altered properties, including, without limitation, improved pharmacokinetic properties and improved clinical efficacy. The invention also encompasses pharmaceutical formulations that comprise these preparations, as well as therapeutic methods that utilize the formulations.

Factor VII Polypeptides and Factor VII-Related Polypeptides

The present invention encompasses human Factor VII polypeptides, such as, e.g., those having the amino acid sequence disclosed in U.S. Pat. No. 4,784,950 (wild-type Factor VII). As used herein, "Factor VII" or "Factor VII polypeptide" encompasses wild-type Factor VII, as well as variants of Factor VII exhibiting substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa that has been chemically modified and Factor VII variants into which specific amino acid sequence alterations have been introduced that modify or disrupt the bioactivity of the polypeptide.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., *J. Biol. Chem.* 272:19919–19924, 1997); (ii) measuring Factor X hydrolysis in an aqueous system (see, Example 5 below); (iii) measuring its physical binding to TF using an instrument based on surface plasmon resonance (Persson, *FEBS Letts.* 413:359–363, 1997) (iv) measuring hydrolysis of a synthetic substrate (see, Example 4 below); and (v) measuring generation of thrombin in a TF-independent in vitro system.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of wild-type Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids. Non-limiting examples of Factor VII variants having substantially the same biological activity as wild-type Factor VII include S52A-FVIIa, S60A-FVIIa (lino et al., *Arch. Biochem. Biophys.* 352: 182–192, 1998); FVIIa variants exhibiting increased proteolytic stability as disclosed in U.S. Pat. No. 5,580,560;Factor VIIa that has been proteolytically cleaved between residues 290 and 291 or between residues 315 and 316 (Mollerup et al., *Biotechnol. Bioeng.* 48:501–505, 1995); and oxidized forms of Factor VIIa (Kornfelt et al., *Arch. Biochem. Biophys.* 363:43–54, 1999). Non-limiting examples of Factor VII variants having substantially reduced or modified biological activity relative to wild-type Factor VII include R152E-FVIIa (wildgoose et al., *Biochem* 29:3413–3420, 1990), S344A-FVIIa (Kazama et al., *J. Biol. Chem.* 270:66–72, 1995), FFR-FVIIa (Holst et al., *Eur. J. Vasc. Endovasc. Surg.* 15:515–520, 1998), and Factor VIIa lacking the Gla domain, (Nicolaisen et al., *FEBS Letts.* 317:245–249, 1993). Non-limiting examples of chemically modified Factor VII polypeptides and sequence variants are described, e.g., in U.S. Pat. No. 5,997,864.

Asparagine-Linked Glycosylation

The present invention provides preparations of Factor VII polypeptides or Factor VII-related polypeptides that comprise a particular spectrum of Factor VII glycoforms, i.e., Factor VII polypeptides or Factor VII-related polypeptides having predetermined patterns of asparagine-linked (N-linked) oligosaccharide chains.

As used herein, a "pattern" of N-linked glycosylation or a glycoform "pattern", "distribution", or "spectrum" refers to the representation of particular oligosaccharide structures within a given population of Factor VII polypeptides or Factor VII-related polypeptides. Non-limiting examples of such patterns include the relative proportion of oligosaccharide chains that (i) have at least one sialic acid residue; (ii) lack any sialic acid residues (i.e., are neutral in charge); (iii) have at least one terminal galactose residue; (iv) have at least one terminal N-acetylgalactosamine residue; (v) have at least one "uncapped" antenna, i.e., have at least one terminal galactose or N-acetylgalactosamine residue; or (vi) have at least one fucose linked $\alpha1 \rightarrow 3$ to an antennary N-acetylglucosamine residue.

As used herein, an oligosaccharide chain refers to the entire oligosaccharide structure that is covalently linked to a single asparagine residue. Factor VII is normally glycosylated at Asn 145 and Asn 322. An N-linked oligosaccharide chain present on Factor VII produced in a human in situ may be bi-, tri-, or tetraantennary, with each antenna having the structure Neu5Ac($\alpha2 \rightarrow 3$ or $\alpha2 \rightarrow 6$)Gal($\beta1 \rightarrow 4$) GlcNAc linked ($\beta1 \rightarrow 2,4$, or 6) to a Man residue which is linked ($\alpha1 \rightarrow 3$ or 6) to Man($\beta1 \rightarrow 4$)GlcNAc($\beta1 \rightarrow 4$)GlcNAc-Asn. (Neu5Ac signifies N-acetylneuraminic acid (sialic acid), Gal signifies galactose, GlcNAc signifies N-acetylglucosamine, and Man signifies mannose). The oligosaccharide chains may also comprise fucose residues, which may be linked $\alpha1 \rightarrow 6$ to GlcNAc. When Factor VII is produced in a human in situ, some of the oligosaccharide chains lack core fucose residues; all of the chains lack antennary fucose residues; and all of the chains are almost completely sialylated, i.e., the terminal sugar of each antenna is N-acetyineuraminic acid linked to galactose via an $\alpha2 \rightarrow 3$ or $\alpha2 \rightarrow 6$ linkage.

When produced in other circumstances, however, Factor VII may contain oligosaccharide chains having different terminal structures on one or more of their antennae, such as, e.g., lacking sialic acid residues; containing N-glycolyineuraminic acid (Neu5Gc) residues; containing a terminal N-acetylgalactosamine (GalNAc) residue in place of galactose; and the like. When produced in, e.g., BHK cells cultured in the presence of calf serum, Factor VII preparations exhibit the following oligosaccharide patterns:

- 87–93% of the oligosaccharide chains contain at least a single sialic acid residue;
- 7–13% are neutral (lack any sialic acid);
- 9–16% contain at least one terminal galactose residue;
- 19–29% contain at least one terminal N-acetylgalactosamine residue; and
- 30–39% contain at least one uncapped antenna, i.e., contain at least one terminal galactose or N-acetylgalactosamine residue.

The present inventors have produced Factor VII preparations containing specific predetermined oligosaccharide patterns that differ from those previously described. The present invention encompasses preparations comprising Factor VII polypeptides or Factor VII-related polypeptides exhibiting one or more of the following glycoform patterns:

(i) Between about 94–100% of the oligosaccharide chains contain at least one sialic acid residue, such as, e.g., between about 94–99%, between about 95–98%, or between about 96–97%. In different embodiments, at least about 94%, 95%, 96%, or 97% of the oligosaccharide chains contain at least one sialic acid residue.

(ii) 6% or less of the oligosaccharide chains are neutral, such as, e.g., between about 1.5–6% or between about 2–4%.

(iii) Less than about 16%, preferably, less than about 10% of the oligosaccharide chains contain at least one terminal galactose, such as, e.g., between about 6–10% or between about 8–9%;

(iv) Less than about 25%, preferably, less than about 10% of the oligosaccharide chains contain at least one terminal GalNAc residue, such as, e.g., between about 6–9% or between about 7–8%;

(v) Less than about 30, preferably, less than about 25% of the oligosaccharide chains contain at least one uncapped antenna, such as, e.g., between about 11–23% or between about 12–18%; and (vi) At least about 2%, preferably, at least about 5%, more preferably, at least about 10% or 20%; and most preferably, at least about 40%, of the oligosaccharide chains contain at least one fucose linked α1→3 to an antennary N-acetylglucosamine residue (i.e., an N-acetylglucosamine residue that is linked β1→2,4, or 6 to a Man residue).

It will be understood that each of (i)–(vi) may represent a distinct glycoform pattern that is encompassed by the present invention, i.e., a preparation according to the invention may be described by only one of (i)–(vi). Alternatively, depending on the particular glycoform pattern, a preparation encompassed by the invention may be described by more than one of (i)–(vi).

Furthermore, a preparation encompassed by the invention may be described by one or more of (i)–(vi) in combination with one or more other structural features. For example, the invention encompasses preparations comprising Factor VII polypeptides or Factor VII-related polypeptides in which the sialic acid residues (Neu5Ac or Neu5Gc) are linked to galactose exclusively in an α2→3 configuration. The invention also encompasses preparations comprising Factor VII polypeptides or Factor VII-related polypeptides that contain fucose linked α 1→6 to a core N-acetylglucosamine and/or fucose linked α1→3 to an antennary N-acetylglucosamine. In one series of embodiments, the preparations of the invention encompass Factor VII or Factor VII-related polypeptides in which more than 99% of the oligosaccharide chains contain at least one sialic acid residue and (a) the sialic acid residues are linked exclusively in an α2→3 configuration and/or (b) there are fucose residues linked to core N-acetylglucosamines and/or (c) a detectable number of antenna terminate in N-acetylgalactosamine. In one embodiment, the invention encompasses preparations comprising wild-type Factor VIIa in which more than 99% of the oligosaccharide chains contain at least one sialic acid residue and the sialic acid residues are linked to galactose exclusively in an α2→3 configuration. In another embodiment, the invention encompasses preparations comprising wild-type Factor VIIa in which more than 99% of the oligosaccharide chains contain at least one sialic acid residue and at least some of the oligosaccharide chains comprise N-acetylgalactosamine. The present invention does not encompass wild-type Factor VII or wild-type Factor VIIa that is isolated from human plasma and is not modified ex vivo by treatment with glycosidases.

In one embodiment, the Factor VIIa preparation comprises oligosaccharide chains having a single fucose linked α1→3 to one antennary N-acetylglucosamine. In another embodiment, the Factor VIIa preparation comprises oligosaccharide chains having fucose residues linked α1→3 to each antennary N-acetylglucosamine of a biantennary oligosaccharide (Sialyl Lewis X structure). In another embodiment, the Factor VIIa preparation comprises oligosaccharide chains having (i) a fucose linked to a core N-acetylglucosamine and (ii) a single fucose linked α1→3 to one antennary N-acetylglucosamine. In another embodiment, the Factor VIIa preparation comprises oligosaccharide chains having (i) a fucose linked to a core N-acetylglucosamine and (ii) fucose residues linked α1→3 to each antennary N-acetylglucosamine of a biantennary oligosaccharide.

In practicing the present invention, the pattern of N-linked oligosaccharides may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anion-exchange (AIE)-HPLC, size-exclusion chromatography (SEC), or MS. See, e.g., Weber et al., *Anal. Biochem.* 225:135 (1995); Klausen et al., *J. Chromatog.* 718:195 (1995); Morris et al., in *Mass Spectrometry of Biological Materials*, McEwen et al., eds., Marcel Dekker, (1990), pp 137–167; Conboy et al., *Biol. Mass Spectrom.* 21:397, 1992; Hellerqvist, *Meth. Enzymol.* 193:554 (1990); Sutton et al., *Anal. Biohcem.* 318:34 (1994); Harvey et al., *Organic Mass Spectrometry* 29:752 (1994).

Following resolution of Factor VII-derived oligosaccharide chains using any of the above methods (or any other method that resolves oligosaccharide chains having different structures), the resolved species are assigned, e.g., to one of groups (i)–(v). The relative content of each of (i)–(v) is calculated as the sum of the oligosaccharides assigned to that group relative to the total content of oligosaccharide chains in the sample.

For example, using AIE-HPLC, 13 or more N-linked oligosaccharide peaks can be resolved from a recombinant Factor VII preparation produced in BHK cells. See, e.g., Klausen et al., *Mol. Biotechnol.* 9:195, 1998. Five of the peaks (designated 1–5 in Klausen et al.) do not contain sialic acid, while eight of the peaks (designated 6, 7, and 10–15) do contain sialic acid.

It will be understood that, in a given analysis, the number and distribution of sialic acid-containing and sialic acid-lacking chains may depend upon (a) the polypeptide being expressed; (b) the cell type and culture conditions; and (c) the method of analysis that is employed, and that the resulting patterns may vary accordingly.

In any case, once the sialic acid-containing oligosaccharides have been resolved from the non-sialic acid-containing oligosaccharides, conventional data analysis programs are used to calculate the area under each peak; the total peak area; and the percentage of the total peak area represented by a particular peak. In this manner, for a given preparation, the sum of the areas of sialic acid-containing peaks/total peak area×100 yields the % sialylation value for the preparation according to the present invention (i.e., the proportion of oligosaccharide chains having at least one sialic acid residue). In a similar manner, the % of chains having no sialic acid or at least one galactose or N-acetylglucosamine can be calculated.

Methods for Producing Factor VII Preparations Having a Predetermined Pattern of N-Linked Oligosaccharides Preparations of Factor VII, Factor VII variants, or Factor VII-related polypeptides, each having a predetermined pattern of N-linked oligosaccharides, may be produced using any appropriate host cell that expresses Factor VII or Factor VII-related polypeptides.

Host Cells: In some embodiments, the host cells are human cells expressing an endogenous Factor VII gene. In these cells, the endogenous gene may be intact or may have been modified in situ, or a sequence outside the Factor VII gene may have been modified in situ to alter the expression of the endogenous Factor VII gene. Any human cell capable of expressing an endogenous Factor VII gene may be used.

In other embodiments, heterologous host cells are programmed to express human Factor VII from a recombinant gene. The host cells may be vertebrate, insect, or fungal cells. Preferably, the cells are mammalian cells capable of the entire spectrum of mammalian N-linked glycosylation; O-linked glycosylation; and γ-carboxylation. See, e.g., U.S. Pat. No. 4,784,950. Preferred mammalian cell lines include the CHO (ATCC CCL 61), COS-1 (ATCC CRL 1650), baby hamster kidney (BHK) and HEK293 (ATCC CRL 1573; Graham et al., *J. Gen. Virol.* 36:59–72, 1977) cell lines. A preferred BHK cell line is the tk⁻ts13 BHK cell line (Waechter and Baserga, *Proc. Natl. Acad. Sci. USA* 79:1106–1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (CHO cell line) (Urlaub and Chasin, *Proc. Natl. Acad. Sci. USA* 77:4216–4220, 1980). (DUKX cells also referred to as CXB11 cells), and DG44 (CHO cell line) (*Cell*, 33:405, 1983, and *Somatic Cell and Molecular Genetics* 12:555, 1986). Also useful are 3T3 cells, Namalwa cells, myelomas and fusions of myelomas with other cells. In a particularly preferred embodiment, the host cells are BHK 21 cells that have been adapted to grow in the absence of serum and have been programmed to express Factor VII. In some embodiments, the cells may be mutant or recombinant cells that express a qualitatively or quantitatively different spectrum of glycosylation enzymes (such as, e.g., glycosyl transferases and/or glycosidases) than the cell type from which they were derived. The cells may also be programmed to express other heterologous peptides or proteins, including, e.g., truncated forms of Factor VII. In one embodiment, the host cells are CHO cells that have been programmed to co-express both the Factor VII polypeptide of interest (i.e., Factor VII or a Factor-VII-related polypeptide) and another heterologous peptide or polypeptide such as, e.g., a modifying enzyme or a Factor VII fragment.

Methods: The present invention encompasses methods for producing a preparation comprising any of the glycoform patterns described above as (i)–(vi) and, in further embodiments, methods for optimizing the glycoform distribution of Factor VII and Factor VII-related polypeptides. These methods are carried out by the steps of:
(a) culturing a cell expressing Factor VII or Factor VII-related polypeptides under a first set of predetermined culture conditions;
(b) recovering Factor VII or Factor VII-related polypeptides from the culture to obtain a preparation comprising the polypeptides; and
(c) analyzing the structure of the oligosaccharides linked to the polypeptides to determine a glycoform pattern.

The methods may further comprise:
(d1) altering the culture conditions of step (a) to achieve a second set of predetermined culture conditions;
(e1) repeating steps (b)–(d1) until a desired glycoform pattern is achieved.

Alternatively, the methods may further comprise
(d2) treating the preparation chemically and/or enzymatically to alter the oligosaccharide structure; and
(e2) repeating steps (b)–(d2) until a desired glycoform pattern is achieved.

These methods may further comprise the step of subjecting preparations having predetermined glycoform patterns to at least one test of bioactivity (including, e.g., clotting, Factor X proteolysis, or TF binding) or other functionality (such as, e.g., pharmacokinetic profile or stability), and correlating particular glycoform patterns with particular bioactivity or functionality profiles in order to identify a desired glycoform pattern.

The variables in the culture conditions that may be altered in step (d1) include, without limitation: the cell of origin, such as, e.g., a cell derived from a different species than originally used; or a mutant or recombinant cell having alterations in one or more glycosyltransferases or glycosidases or other components of the glycosylation apparatus (see, Grabenhorst et al., *Glycoconjugate J.* 16:81, 1999; Bragonzi et al., *Biochem. Biophys. Acta* 1474:273, 2000; Weikert, *Nature Biotechnol.* 17:1116, 1999); the level of expression of the polypeptide; the metabolic conditions such as, e.g., glucose or glutamine concentration; the absence or presence of serum; the concentration of vitamin K; protein hydrolysates, hormones, trace metals, salts as well as process parameters like temperature, dissolved oxygen level and pH.

The enzymatic treatments that may be used in step (d2) to modify the oligosaccharide pattern of a preparation include, without limitation, treatment with one or more of sialidase (neuraminidase), galactosidase, fucosidase; galactosyl transferase, fucosyl transferase, and/or sialyltransferase, in a sequence and under conditions that achieve a desired modification in the distribution of oligosaccharide chains having particular terminal structures. Glycosyl transferases are commercially available from Calbiochem (La Jolla, Calif.) and glycosidases are commercially available from Glyko, Inc., (Novato, Calif.).

In one series of embodiments, host cells expressing Factor VII or a related polypeptide are subjected to specific culture conditions in which they secrete glycosylated Factor VII polypeptides having the desired pattern of oligosaccharide structures described above as any of (i)–(vi). Such culture conditions include, without limitation, a reduction in, or complete absence of, serum. Preferably, the host cells are adapted to grow in the absence of serum and are cultured in the absence of serum both in the growth phase and in the production phase. Such adaptation procedures are described, e.g., in Scharfenberg, et al., *Animal Cell Technology Developments towards the 21$^{st}$ Century*, E. C. Beuvery et al. (Eds.), Kluwer Academic Publishers, pp. 619–623, 1995 (BHK and CHO cells); Cruz, *Biotechnol. Tech.* 11:117–120, 1997 (insect cells); Keen, *Cytotechnol.* 17:203–211, 1995 (myeloma cells); Berg et al., *Biotechniques* 14:972–978, 1993 (human kidney 293 cells). In a preferred embodiment, the growth medium that is added to the cells contains no protein or other component that was isolated from an animal tissue or an animal cell culture. See, e.g., Example 1 below. Typically, in addition to conventional components, a medium suitable for producing Factor VII contains Vitamin K at a concentration between 0.1–50 mg/liter, which is required for γ-carboxylation of glutamine residues in Factor VII.

In another series of embodiments, the glycoforms of the invention are produced by subjecting a preparation of Factor VII or Factor VII-related polypeptides to enzymatic and/or chemical modification of the N-linked oligosaccharides contained therein.

Factor VII Preparations

As used herein, a "Factor VII preparation" refers to a plurality of Factor VII polypeptides, Factor VIIa polypeptides, or Factor VII-related polypeptides, including variants and chemically modified forms, that have been separated from the cell in which they were synthesized.

Separation of polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., *J. Biol. Chem.* 261:11097, 1986; and Thim et al., *Biochem.* 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J. -C. Janson and Lars Ryden, editors, VCH Publishers, New York, 1989. Following purification, the preparation preferably contains less than about 10% by weight, more preferably less than about 5% and most preferably less than about 1%, of non-Factor VII proteins derived from the host cell.

Factor VII and Factor VII-related polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like. The resulting activated Factor VII may then be formulated and administered as described below.

Functional Properties of Factor VII Preparations

The preparations of Factor VII polypeptides and Factor VII-related polypeptides having predetermined oligosaccharide patterns according to the invention exhibit improved functional properties relative to reference preparations. The improved functional properties may include, without limitation, a) physical properties such as, e.g., storage stability; b) pharmacokinetic properties such as, e.g., bioavailability and half-life; and c) immunogenicity in humans.

A reference preparation refers to a preparation comprising a polypeptide that is identical to that contained in the preparation of the invention to which it is being compared (such as, e.g., wild-type Factor VII or a particular variant or chemically modified form) except for exhibiting a different pattern of asparagine-linked glycosylation. For example, reference preparations typically comprise one or more of the following glycoform patterns: (i) less than about 93% (such as, e.g. less than about 92% or less than about 90%) of the oligosaccharide chains contain at least one sialic acid residue; (ii) at least about 6% (such as, e.g., at least about 7.5% or at least about 10%) of the oligosaccharide chains lack any sialic acid (i.e., are neutral); (iii) at least about 10% (such as, e.g., at least about 12.5% or at least about 15%) of the oligosaccharide chains contain at least one terminal galactose residue; (iv) at least about 15% (such as, e.g., at least about 20% or at least about 25%) of the oligosaccharide chains contain at least one terminal N-acetylgalactosamine residue; (v) at least about 25% (such as, e.g., at least about 30% or at least about 35%) of the oligosaccharide chains contain at least one uncapped antenna (i.e., contain at least one terminal galactose or N-acetylgalactosamine residue); or (vi) essentially undetectable levels (such as, e.g., less than about 0.2%) of antennary fucose residues.

Storage stability of a Factor VII preparation may be assessed by measuring (a) the time required for 20% of the bioactivity of a preparation to decay when stored as a dry powder at 25° C. and/or (b) the time required for a doubling in the proportion of Factor VIIa aggregates in the preparation.

In some embodiments, the preparations of the invention exhibit an increase of at least about 30%, preferably at least about 60% and more preferably at least about 100%, in the time required for 20% of the bioactivity to decay relative to the time required for the same phenomenon in a reference preparation, when both preparations are stored as dry powders at 25° C. Bioactivity measurements may be performed using any of a clotting assay, proteolysis assay, TF-binding assay, or TF-independent thrombin generation assay.

In some embodiments, the preparations of the invention exhibit an increase of at least about 30%, preferably at least about 60%, and more preferably at least about 100%, in the time required for doubling of aggregates relative to a reference preparation, when both preparations are stored as dry powders at 25° C. The content of aggregates is determined by gel permeation HPLC on a Protein Pak 300 SW column (7.5×300 mm) (Waters, 80013) as follows. The column is equilibrated with Eluent A (0.2 M ammonium sulfate, 5% isopropanol, pH adjusted to 2.5 with phosphoric acid, and thereafter pH is adjusted to 7.0 with triethylamine), after which 25 $\mu$g of sample is applied to the column. Elution is with Eluent A at a flow rate of 0.5 ml/min for 30 min, and detection is achieved by measuring absorbance at 215 nm. The content of aggregates is calculated as the peak area of the Factor VII aggregates/total area of Factor VII peaks (monomer and aggregates).

"Bioavailability" refers to the proportion of an administered dose of a Factor VII or Factor VII-related preparation that can be detected in plasma at predetermined times after administration. Typically, bioavailability is measured in test animals by administering a dose of between about 25–250 $\mu$g/kg of the preparation; obtaining plasma samples at predetermined times after administration; and determining the content of Factor VII or Factor VII-related polypeptides in the samples using one or more of a clotting assay (or any bioassay), an immunoassay, or an equivalent. The data are typically displayed graphically as [Factor VII] v. time and the bioavailability is expressed as the area under the curve (AUC). Relative bioavailability of a test preparation refers to the ratio between the AUC of the test preparation and that of the reference preparation.

In some embodiments, the preparations of the present invention exhibit a relative bioavailability of at least about 110%, preferably at least about 120%, more preferably at least about 130% and most preferably at least about 140% of the bioavailability of a reference preparation. The bioavailability may be measured in any mammalian species, preferably dogs, and the predetermined times used for calculating AUC may encompass different increments from 10 min–8 h.

"Half-life" refers to the time required for the plasma concentration of Factor VII polypeptides of Factor VII-related polypeptides to decrease from a particular value to half of that value. Half-life may be determined using the same procedure as for bioavailability. In some embodiments, the preparations of the present invention exhibit an increase in half-life of at least about 0.25 h, preferably at least about 0.5 h, more preferably at least about 1 h, and most preferably at least about 2 h, relative to the half-life of a reference preparation.

"Immunogenicity" of a preparation refers to the ability of the preparation, when administered to a human, to elicit a deleterious immune response, whether humoral, cellular, or both. Factor VIIa polypeptides and Factor VIIa-related polypeptides are not known to elicit detectable immune responses in humans. Nonetheless, in any human sub-population, there may exist individuals who exhibit sensitivity to particular administered proteins. Immunogenicity may be measured by quantifying the presence of anti-Factor VII antibodies and/or Factor VII-responsive T-cells in a sensitive individual, using conventional methods known in the art. In some embodiments, the preparations of the present invention exhibit a decrease in immunogenicity in a sensitive individual of at least about 10%, preferably at least about 25%, more preferably at least about 40% and most preferably at least about 50%, relative to the immunogenicity for that individual of a reference preparation.

Pharmaceutical Compositions and Methods of Use

The preparations of the present invention may be used to treat any Factor VII-responsive syndrome, such as, e.g., bleeding disorders, including, without limitation, those caused by clotting factor deficiencies (e.g., haemophilia A and B or deficiency of coagulation factors Xl or VII); by thrombocytopenia or von Willebrand's disease, or by clotting factor inhibitors, or excessive bleeding from any cause. The preparations may also be administered to patients in association with surgery or other trauma or to patients receiving anticoagulant therapy.

Preparations comprising Factor VII-related polypeptides according to the invention, which have substantially reduced bioactivity relative to wild-type Factor VII, may be used as anticoagulants, such as, e.g., in patients undergoing angioplasty or other surgical procedures that may increase the risk of thrombosis or occlusion of blood vessels as occurs, e.g., in restenosis. Other medical indications for which anticoagulants are prescribed include, without limitation, deep vein thrombosis, pulmonary embolism, stroke, disseminated intravascular coagulation (DIC), fibrin deposition in lungs and kidneys associated with gram-negative endotoxemia, myocardial infarction; Acute Respiratory Distress Syndrome (ARDS), Systemic Inflammatory Response Syndrome (SIRS), Hemolytic Uremic Syndrome (HUS), MOF, and TTP.

Pharmaceutical compositions comprising the Factor VII and Factor VII-related preparations according to the present are primarily intended for parenteral administration for prophylactic and/or therapeutic treatment. Preferably, the pharmaceutical compositions are administered parenterally, i.e., intravenously, subcutaneously, or intramuscularly. They may be administered by continuous or pulsatile infusion.

Pharmaceutical compositions or formulations comprise a preparation according to the invention in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

The concentration of Factor VII or Factor VII-related polypeptides in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the preparation. Actual methods for preparing parenterally administrable compositions will be known or apparent to those skilled in the art and are described in more detail in, for example, *Remington's Pharmaceutical Sciences,* 18th ed., Mack Publishing Company, Easton, Pa. (1990).

The compositions containing the preparations of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". Effective amounts for each purpose will depend on the severity of the disease or injury as well as the weight and general state of the subject. In general, however, the effective amount will range from about 0.05 mg up to about 500 mg of the preparation per day for a 70 kg subject, with dosages of from about 1.0 mg to about 200 mg of the preparation per day being more commonly used. It will be understood that determining an appropriate dosage may be achieved using routine experimentation, by constructing a matrix of values and testing different points in the matrix.

Local delivery of the preparations of the present invention, such as, for example, topical application, may be carried out, e.g., by means of a spray, perfusion, double balloon catheters, stent, incorporated into vascular grafts or stents, hydrogels used to coat balloon catheters, or other well established methods. In any event, the pharmaceutical compositions should provide a quantity of the preparation sufficient to effectively treat the subject.

The pharmaceutical compositions of the invention may further comprise other bioactive agents, such as, e.g., non-Factor VII-related coagulants or anticoagulants.

The following examples are intended as non-limiting illustrations of the present invention.

EXAMPLE 1

Production and Analysis of a Factor VII Preparation Exhibiting an Altered Glycoform Pattern The following experiment was performed to produce a Factor VII preparation having an altered glycoform pattern.

I. Production:

A BHK cell line transformed with a Factor VII-encoding plasmid was adapted to growth in suspension culture in the absence of serum. The cells were propagated sequentially in spinner cultures and as the cell number increased, the volume was gradually increased by addition of new medium.

Finally, 6 l of seed culture were inoculated into a 100-liter production bioreactor containing macroporous Cytopore 1 carriers (Pharmacia), after which the suspension cells became immobilized in the carriers. The culture was maintained at 36° C. at a pH of 6.7–6.9 and a DO of 50%. The volume in the production bioreactor was gradually increased by addition of new medium as the cell number increased. When the cell density reached approximately $2 \times 10^6$ cells/ml, the production phase was initiated and a medium change was performed every 24 hours: Agitation was stopped to allow for sedimentation of the cell-containing carriers, and 80% of the culture supernatant was then harvested and replaced with new medium. The harvested culture supernatant was filtered to remove non-trapped cells and cell debris and was then transferred for further processing.

During the production phase the cells reached $3–6 \times 10^6$ cells/ml and a titer of 2–7 mg Factor VII/liter.

II. Analysis of the Glycoform Pattern of Recombinant Factor VII

The oligosaccharide patterns of the following preparations were compared: (a) recombinant Factor VII preparations produced as described in part I (n=7); and two reference preparations: (b) recombinant Factor VII preparations produced in BHK cells in the presence of calf serum (n=10); and (c) a Factor VII preparation purified from human plasma.

The N-linked oligosaccharides were released from the polypeptides by chemical cleavage (hydrazinolysis, on a GlycoPrep1000 unit, Oxford GlycoSciences) or by enzymatic cleavage (N-glycosidase F from, eg., Boehringer Mannheim). The released oligosaccharides were labeled with 2-aminobenzamide (using a signal labelling kit, K-404, Oxford GlycoSciences or Glyko). The labeled oligosaccharides were analysed using anion-exchange HPLC on a CarboPac PA100 column (4×250 mm, Dionex, P/N 43055) with a Guard column (4×50 mm, Dionex, P/N 43054). The column was equilibrated with 150 mM sodium hydroxide and eluted with a gradient of 0–150 mM sodium acetate, 150 mM sodium hydroxide. Oligosaccharides were detected using fluorescence, with excitation at 330 nm and emission at 420 nm.

The relative contents of the various Factor VII oligosaccharide structures (Klausen et al., 1998) were calculated as the relative peak areas for the carbohydrate peaks in the anion-exchange HPLC analysis. Based on the structural elements of each oligosaccharide, it was assigned to one of the following: (i) chains containing at least one sialic acid; (ii) chains lacking any sialic acid (i.e., neutral); (iii) chains containing at least one terminal galactose residue; (iv) chains containing at least one terminal N-acetylgalactosamine residue; and (v) chains containing at least one uncapped antenna (i.e., at least one terminal galactose or N-acetylgalactosamine residue). Finally, the sum of the relative contents of the oligosaccharide chains assigned to each group was calculated as a percentage of the total oligosaccharide chains. The standard deviation of this determination was calculated to be 0.08% (intraday variation); 0.7% (day-to-day variation); and 0.5% (1–100 µg interval).

The resulting glycoform patterns are illustrated in the following table:

|   | (i) | (ii) | (iii) | (iv) | (v) |
|---|---|---|---|---|---|
| a | 93.1–98.7 | 1.3–6.9 | 5.9–16.4 | 5.9–8.7 | 11.7–23.9 |
| b | 88.3–92.5 | 7.5–12.9 | 9.4–16.8 | 19.0–28.6 | 30.1–39.0 |
| c | 99.5% | <0.5% | 2–3% | 0% | 2–3% |

The recombinant Factor VII preparations produced according to this Example (i.e., in the absence of serum) exhibit a glycoform pattern that differs from both the glycoform pattern of recombinant Factor VII produced in the presence of serum and native Factor VII isolated from human plasma. The oligosaccharides of recombinant Factor VII produced in the absence of serum are sialylated to a higher extent than those produced in the presence of serum and contain less neutral chains and less chains that terminate in either galactose or N-acetylgalatosamine.

III. Bioavailability

The following experiment was performed to compare the bioavailability of two Factor VII preparations produced as above (I and II) with that of two reference Factor VII preparations (i.e., produced in the presence of serum) (A and B).

Groups of 8 rats were administered either a test preparation or a reference preparation at a dose of 25 µg/kg (≈100 µg/rat) in a glycylglycine buffer (pH 7.4) containing sodium chloride (7.87 mg/ml), calcium chloride dihydrate (1.48 mg/ml), mannitol (2.5 mg/ml) and polysorbate 80. Blood samples were withdrawn at 10 min and 30 min following the initial administration. Plasma was obtained from the samples and Factor VII was quantified by ELISA. Bioavailability of each sample is expressed as the dose-adjusted area under the plasma concentration curve for Factor VII based on the 10 and 30-min samples ($AUC_{10-30}$/dose). The relative bioavailability is expressed as the ratio between the mean $AUC_{10-30}$/dose of the test and reference samples×100. The 90% confidence limits for the relative bioavailability were calculated from the 90% confidence limits for differences between preparations.

The results are summarized in the Table below. (The % sialylation of each preparation, which was measured as described above, is indicated in parentheses).

| test | reference | relative bioavailability | 90% conf. lower | 90% conf. upper |
|---|---|---|---|---|
| I (97.5%) | A (93%) | 128.6 | 116.1 | 141.1 |
| I (97.5%) | B (86%) | 154.9 | 141.2 | 168.5 |
| II (96.7%) | A 93% | 117.3 | 104.8 | 129.8 |
| II (96.7%) | B (86%) | 141.2 | 127.5 | 154.8 |

The results indicate that even relatively small differences in the proportion of oligosaccharide chains having at least one sialic acid residue, such as, e.g., between 93% and 96 or 97%, can have a marked impact on bioavailability (increase of 20–30%). A 10% increase in the % sialylation, moreover, causes a 40–50% increase in bioavailability.

EXAMPLE 2

Analysis of Factor VII Preparations Exhibiting an Altered Glycoform Pattern

Factor VII was produced as described in Example 1 above, with the exception that the Factor VII was harvested from 500-l cultures. Glycoform analysis was performed as described in Example 1. Three independent preparations (A, B, and C) were analyzed and compared with a reference preparation (D).

Bioavailability was measured in a dog model as follows: The experiment was performed as a four leg cross-over study in 12 Beagle dogs divided in four groups. All animals received each of the three test preparations A, B, and C and the reference preparation D at a dose of ≈90 µg/kg in a glycylglycine buffer (pH 5.5) containing sodium chloride (2.92 mg/ml), calcium chloride dihydrate (1.47 mg/ml), mannitol (30 mg/ml) and polysorbate 80. Blood samples were withdrawn at 10, 30, and 60 minutes and 2, 3, 4, 6 and 8 hours following the initial administration. Plasma was obtained from the samples and Factor VII was quantified by ELISA.

Bioavailability of each sample is expressed as the dose-adjusted area under the plasma concentration curve for Factor VII (AUC/dose). The relative bioavailability is expressed as the ratio between the mean AUC/dose of the test and reference preparation×100 and 90% confidence limits for the relative bioavailability were calculated.

The results are summarized in the Table below. The % sialylation of each preparation, which was measured as described in Example 1 above, is indicated in parentheses.

| Test | Reference | Relative bioavailability | 90% conf. limit lower | 90% conf. limit upper |
| --- | --- | --- | --- | --- |
| A (98.7%) | D (88.2%) | 144 | 135 | 153 |
| B (95.9%) | D (88.2%) | 127 | 119 | 136 |
| C (93.1%) | D (88.2%) | 112 | 105 | 120 |

The results indicate that small differences in the proportion of oligosaccharide chains having at least one sialic acid residue have a marked impact on bioavailability of Factor VII. A 10% increase in the % sialylation causes a 30–50% increase in bioavailability with a close to linear relationship for the three test preparations and the reference preparation

EXAMPLE 3

Factor VII Preparations Exhibiting an Altered Glycoform Pattern

The following experiment was performed to produce a Factor VII preparation having an altered glycoform pattern.

I. Construction of Cell Line and Factor VII Production

A plasmid vector pLN174 for expression of human FVII has been described (Persson and Nielsen. 1996. *FEBS Lett.* 385: 241–243). Briefly, it carries the cDNA nucleotide sequence encoding human FVII including the propeptide under the control of a mouse metallothionein promoter for transcription of the inserted cDNA, and mouse dihydrofolate reductase cDNA under the control of an SV40 early promoter for use as a selectable marker.

For construction of a plasmid vector encoding a gamma-carboxylation recognition sequence, a cloning vector (pBluescript II KS+, Stratagene) containing cDNA encoding FVII including its propeptide was used (pLN171). (Persson et al. 1997. *J. Biol. Chem.* 272: 19919–19924). A nucleotide sequence encoding a stop codon was inserted into the cDNA encoding FVII after the propeptide of FVII by inverse PCR-mediated mutagenesis using this cloning vector. The template plasmid was denatured by treatment with NaOH followed by PCR with Pwo (Boehringer-Mannheim) and Taq (Perkin-Elmer) polymerases with the following primers:

a) 5'-AGC GTT TTA GCG CCG GCG CCG GTG CAG GAC-3' (SEQ ID NO. 1)

b) 5'-CGC CGG CGC TAA AAC GCT TTC CTG GAG GAG CTG CGG CC-3' (SEQ ID NO. 2)

The resulting mix was digested with DpnI to digest residual template DNA and *Escherichia coli* were transformed with the PCR product. Clones were screened for the presence of the mutation by sequencing. The cDNA from a correct clone was transferred as a BamHI-EcoRI fragment to the expression plasmid pcDNA3 (Invitrogen). The resulting plasmid was termed pLN329. CHO K1 cells (ATCC CCI61) were transfected with equal amounts of pLN174 and pLN329 with the Fugene6 method (Boehriner-Mannheim). Transfectants were selected by the addition of methotrexate to 1 µM and G418 to 0.45 mg/ml. The pool of transfectants were cloned by limiting dilution and FVII expression from the clones was measured.

A high producing clone was further subcloned and a clone E11 with a specific FVII expression of 2.4 pg/cell/day in Dulbecco-modified Eagle's medium with 10% fetal calf serum was selected. The clone was adapted to serum free suspension culture in a commercially available CHO medium (JRH Bioscience) free of animal derived components.

The adapted cells were propagated sequentially in spinner cultures and as the cell number increased, the volume was gradually increased by addition of new medium. After 25 days, 6 l of spinner culture were inoculated into a 50-liter bioreactor. The cells were propagated in the bioreactor and as the cell number increased, the volume was gradually increased by addition of new medium.

Finally, 50 l of seed culture were inoculated into a 500-liter production bioreactor containing macroporous Cytopore 1 carriers (Pharmacia), after which the suspension cells became immobilized in the carriers. The culture was maintained at 36° C. at a pH of 7.0–7.1 and a Dissolved Oxygen Tension (DOT) of 50% of saturation. The volume in the bioreactor was gradually increased by addition of new medium as the cell number increased. When the cell density reached approximately 10–12×10⁵ cells/ml, the production phase was initiated and a medium change was performed every 24 hours: agitation was stopped to allow for sedimentation of the cell-containing carriers, and 80% of the culture supernatant was then harvested and replaced with new medium. The harvested culture supernatant was filtered to remove non-trapped cells (i.e. cells that were not immobilized in carriers) and cell debris and was then transferred for further processing.

During the production phase the cells reached 2–3×10⁷ cells/ml and a titer of 8 mg Factor VII/liter.

II. Glycoform Analysis

A. The oligosaccharide pattern of a Factor VII preparation produced as described above (a) was compared with those of (b) recombinant Factor VII preparations produced in BHK cells in the presence of calf serum and (c) a Factor VII preparation purified from human plasma. The methods used were essentially as described in Example 1.

The results are shown in the Table below. The oligosaccharide assignments are as follows: (i) chains containing at least one sialic acid; (ii) chains lacking any sialic acid (i.e., neutral); (iii) chains containing at least one terminal galactose residue; (iv) chains containing at least one terminal N-acetylgalactosamine residue; and (v) chains containing at least one uncapped antenna (i.e., at least one terminal galactose or N-acetylgalactosamine residue).

|   | (i) | (ii) | (iii) | (iv) | (v) |
|---|---|---|---|---|---|
| A | 95.2 | 4.8 | 22.9 | 0.1 | 23.0 |
| B | 88.3–92.5 | 7.5–12.9 | 9.4–16.8 | 19.0–28.6 | 30.1–39.0 |
| C | 99.5% | <0.5% | 2–3% | 0% | 2–3% |

B. The oligosaccharide patterns of five independent Factor VII preparations produced as described in this Example (a) were compared with those of (b) recombinant Factor VII preparations produced in BHK cells in the presence of calf serum and (c) a Factor VII preparation purified from human plasma, using the analytical methods described in Example 1.

Based on the structural elements of each oligosaccharide, it was assigned to one of the following: (i) chains containing at least one sialic acid; (ii) chains lacking any sialic acid (i.e., neutral); (iii) chains containing at least one fucose linked to the antenna. Finally, the sum of the relative contents of the oligosaccharide chains assigned to each group was calculated as a percentage of the total oligosaccharide chains. The standard deviation of this determination was calculated to be 0.08% (intraday variation); 0.7% (day-to-day variation); and 0.5% (1–100 μg interval).

The resulting glycoform patterns are illustrated in the following Table:

|   | (i) | (ii) | (iii) |
|---|---|---|---|
| A | 89.0–97.9% | 2.1–11.0% | 6.3–21.3% |
| B | 88.3–92.5% | 7.5–12.9% | 0% |
| C | 99.5% | <0.5% | 0% |

The recombinant Factor VII preparations produced according to Example 1 (i.e., produced in the absence of serum by the CHO cell line) exhibit a glycoform pattern that differs from both the glycoform pattern of recombinant Factor VII produced in the presence of serum and native Factor VII isolated from human plasma. The oligosaccharides of recombinant Factor VII produced in the absence of serum by the CHO 282.4 cell line include structures with fucose linked to the antenna, which are absent from both of the reference preparations. Two of the structures have been purified and characterized by matrix assisted laser desorption ionisation mass spectrometry, by treatment with linkage specific fucosidase enzymes and by anion-exchange HPLC as described above. The two structures have been shown to contain the sialyl Lewis xstructure, i.e., fucose linked $\alpha 1 \rightarrow 3$ to an antennary N-acetylglucosamine in a sialylated oligosaccharide.

III. Bioactivity

Five Factor VII preparations produced as described in this Example were analyzed for (a) thrombin generation and (b) binding to tissue factor (TF) and compared with recombinant Factor VII produced in BHK cells in the presence of serum (reference). The following Table correlates the glycoform patterns (% of oligosaccharide chains containing sialic acid and the % containing fucosylated antenna) and the two bioactivities.

| Factor VII Preparation | Oligosaccharide Pattern | | Thrombin generation (% of reference) | TF binding Kd (nM) |
|---|---|---|---|---|
| | % Sialyl | % Fucosyl | | |
| 1 | 98 | 6 | 125 | 2.8 |
| 2 | 94 | 13 | 123 | 2.0 |
| 3 | 93 | 14 | 126 | 1.8 |
| 4 | 88 | 16 | 145 | 3.3 |
| 5 | 86 | 21 | 158 | 2.8 |
| reference | 86–93 | 0 | 100 | 2.2–6.6 |

The results indicate that Factor VII preparations having fucosylated antennae exhibit higher TF-independent Factor VII activity (as exhibited, e.g. by thrombin generation) than Factor VII preparations lacking fucosylated antennae.

EXAMPLE 4

In Vitro Hydrolysis Assay

The following method can be used to assay Factor VIIa bioactivity. The assay is carried out in a microtiter plate (MaxiSorp, Nunc, Denmark). The chromogenic substrate D-Ile-Pro-Arg-p-nitroanilide (S-2288, Chromogenix, Sweden), at a final concentration of 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of a test and a reference Factor VIIa.

EXAMPLE 5

In Vitro Proteolysis Assay

The following method can be used to assay Factor VIIa bioactivity. The assay is carried out in a microtiter plate (MaxiSorp, Nunc, Denmark). Factor VIIa (10 nM) and Factor X (0.8 microM) in 100 μl 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 μl 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of a test and a reference Factor VIIa.

All patents, patent applications, and literature references referred to herein are hereby incorporated by reference in their entirety.

Many variations of the present invention will suggest themselves to those skilled in the art in light of the above detailed description. Such obvious variations are within the full intended scope of the appended claims.

What is claimed is:

1. A preparation comprising a plurality of Factor VII polpeptides or Factor VII-related polypeptides produced in Chinese Hamster Ovary-K1 (CHO-K1) cells in the absence of serum, wherein said cells are adapted to grow in the absence of serum and are cultured in the absence of serum both in the growth phase and in the production phase.

2. A preparation as defined in claim 1, wherein the Factor VII polypeptides are selected from the group consisting of: human S52A-Factor VII, human S60A-Factor VII, human Factor VII that has been proteolytically cleaved between residues 290 and 291; human Factor VII that has been proteolytically cleaved between residues 315 and 316; and Factor VII that has been oxidized, wherein wild-type human Factor VII has the sequence of SEQ ID NO:3.

3. A preparation as defined in claim 1, wherein the human Factor VII-related polypeptides are selected from the group consisting of: R152E-Factor VII, S344A-Factor VII, FFR-Factor VII, and Factor VIIa lacking the Gla domain, wherein wild-type human Factor VII has the sequence of SEQ ID NO:3.

4. A preparation as define in claim 1, wherein the preparation exhibits a bioavailability that is at least 110% of the bioavailability of a reference preparation, wherein the oligosaccharides of the reference preparation lack fucose linked α1→3 to an antennary N-acetylglucosamine.

5. A preparation as defined in claim 4, wherein the preparation exhibits a bioavailability that is at least 120% of the bioavailability of a reference preparation.

6. A preparation as defined in claim 4, wherein the preparation exhibits a bioavailability that is at least 130% of the bioavailability of a reference preparation.

7. A preparation as defined in claim 4, wherein the preparation exhibits a bioavailability that is at least 140% of the bioavailability of a reference preparation.

8. A preparation as defined in claim 1, wherein the preparation exhibits tissue factor-independent thrombin generating activity that is at least 110% that of a reference preparation, wherein the oligosaccharides of the reference preparation lack fucose linked α1→3 to an antennary N-acetylglucosamine.

9. A preparation as defined in claim 1, wherein the preparation exhibits a bioavailability that is at least 110% of the bioavailability of a reference preparation, wherein less than about 93% of the oligosaccharide chains in the reference preparation comprise at least one sialic acid moiety.

10. A pharmaceutical formulation comprising a preparation as defined in claim 1 and pharmaceutically acceptable carrier or adjuvant.

11. A method for treating a Factor VII-responsive syndrome, the method comprising administering a pharmaceutical formulation as defined in claim 10 to a patient in need of such treatment, under conditions that result in a decrease in bleeding and/or an increase in blood clotting.

12. A method as defined in claim 11, wherein the syndrome is selected from the group consisting of haemophilia A, haemophilia B, Factor XI deficiency, Factor VII deficiency, thrombocytopenia, von Willebrand's disease, presence of clotting factor inhibitor, surgery, trauma, and anticoagulant therapy.

13. A method for decreasing bleeding and/or increasing clotting, the method comprising administering a pharmaceutical formulation as defined in claim 10 to a patient in need of such treatment, under conditions that result in a decrease in bleeding and/or an increase in blood clotting.

14. A method for producing a prepararation comprising Factor VII polypeptides or Factor VII-related polypeptides having a predetermined pattern of N-linked glycosylation, said method comprising culturing a Chinese Hamster Ovary-K1 (CHO-K1) cell that has been adapted to grow in the absence of serum in a medium lacking serum for both growth and production phases.

15. A preparation comprising a plurality of Factor VII polypeptides or Factor VII-related polypeptides produced in Chinese Hamster Ovary-K1 (CHO-K1) cells in the absence of animal-derived components, wherein said cells are adapted to grow in the absence of animal-derived components and are cultured in the absence of animal-derived components both in the growth phase and in the production phase.

16. A preparation as defined in claim 15, wherein the human Factor VII-related polypeptides are selected from the group consisting of: R152E-Factor VII, S344A-Factor VII, FFR-Factor VII, and Factor VIIa lacking the Gla domain, wherein wild-type human Factor VII has the sequence of SEQ ID NO:3.

17. A preparation as defined in claim 15, wherein the preparation exhibits a bioavailabiity that is at least 110% of the bioavailabity of a reference preparation, wherein the oligosaccharides of the reference preparbtion lack fucose linked α1→3 to an antennary N-acetylglucosamine.

18. A preparation as defined in claim 17, wherein the preparation exhibits bioavailability that least 120% of bioavailability of a reference preparation.

19. A preparation as defined in claim 18, wherein the preparation exhibits a bioavailability that is at least 130% of the bioavailability of a reference preparation.

20. A preparation as defined in claim 19, wherein the preparation exhibits a bioavailability that is at least 140% of the bioavailability of a reference preparation.

21. A preparation as defined in claim 15, wherein the preparation exhibits tissue factor-independent thrombin generating activity that is at least 110% that of a reference preparation, wherein the oligosaccharides of the reference preparation lack fucose linked α1→3 to an antennary N-acetylglucosamine.

22. A preparation as defined in claim 15, wherein the preparation exhibits a bioavailability that is at least 110% of the bioavailability of a reference preparation, wherein less than about 93% of the oligosaccharide chains in the reference preparation comprise at least one slalic acid moiety.

23. A pharmaceutical formulation comprising a preparation as defined in claim 15 and a parmaceutically acceptable carrier or adjuvant.

24. A method for treating a Factor VII-responsive syndrome, the method comprising administering a pharmaceutical formulation as defined in claim 23 to a patient in need of such treatment, under conditions that result in a decrease in bleeding and/or an increase in blood clotting.

25. A method as defined in claim 24, wherein the syndrome is selected from the group consisting of haemophilia A, haemophilia B, Factor XI deficiency, Factor VII deficiency, thrombocytopenia, von Willebrand's disease, presence of clotting factor inhibitor, surgery, trauma, and anticoagulant therapy.

26. A method for decreasing bleeding and/or increasing clotting, the method comprising administering a pharmaceutical formulation as defined in claim 23 to a patient in need of such treatment, under conditions that result in a decrease in bleeding and/or an increase in blood clotting, wherein the formulation comprises Factor VII polypeptides.

27. A method for producing a preparation comprising Factor VII polypeptides or Factor VII-related polypeptides having a predetermined pattern of N-linked glycosylation, said method comprising culturing a Chinese Hamster Ovary-K1 (CHO-K1) cell that has been adapted to grow in the absence of animal-derived components in a medium lacking animal-derived components for both growth and production phases.

* * * * *

SEQUENCE LISTING

<160> NUMBER OF SEQ ID NOS: 3

<210> SEQ ID NO 1
<211> LENGTH: 30
<212> TYPE: DNA
<213> ORGANISM: Artificial
<220> FEATURE:
<223> OTHER INFORMATION: Synthetic

<400> SEQUENCE: 1
agcgttttag cgccggcgcc ggtgcaggac                                              30

<210> SEQ ID NO 2
<211> LENGTH: 38
<212> TYPE: DNA
<213> ORGANISM: Artificial
<220> FEATURE:
<223> OTHER INFORMATION: Synthetic

<400> SEQUENCE: 2
cgccggcgct aaaacgcttt cctggaggag ctgcggcc                                     38

<210> SEQ ID NO 3
<211> LENGTH: 406
<212> TYPE: PRT
<213> ORGANISM: Homo sapiens
<220> FEATURE:
<221> NAME/KEY: MISC FEATURE
<222> LOCATION: (1)..(406)
<223> OTHER INFORMATION: Xaa=Gamma Carboxyglutamic Acid

<400> SEQUENCE: 3

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

-continued

```
Gly Glu His Asp Leu Ser Glu His Asp Gly Asp Glu Gln Ser Arg Arg
    210                 215                 220
Val Ala Gln Val Ile Ile Pro Ser Thr Tyr Val Pro Gly Thr Thr Asn
225                 230                 235                 240
His Asp Ile Ala Leu Leu Arg Leu His Gln Pro Val Val Leu Thr Asp
                245                 250                 255
His Val Val Pro Leu Cys Leu Pro Glu Arg Thr Phe Ser Glu Arg Thr
                260                 265                 270
Leu Ala Phe Val Arg Phe Ser Leu Val Ser Gly Trp Gly Gln Leu Leu
                275                 280                 285
Asp Arg Gly Ala Thr Ala Leu Glu Leu Met Val Leu Asn Val Pro Arg
        290                 295                 300
Leu Met Thr Gln Asp Cys Leu Gln Gln Ser Arg Lys Val Gly Asp Ser
305                 310                 315                 320
Pro Asn Ile Thr Glu Tyr Met Phe Cys Ala Gly Tyr Ser Asp Gly Ser
                325                 330                 335
Lys Asp Ser Cys Lys Gly Asp Ser Gly Gly Pro His Ala Thr His Tyr
                340                 345                 350
Arg Gly Thr Trp Tyr Leu Thr Gly Ile Val Ser Trp Gly Gln Gly Cys
            355                 360                 365
Ala Thr Val Gly His Phe Gly Val Tyr Thr Arg Val Ser Gln Tyr Ile
    370                 375                 380
Glu Trp Leu Gln Lys Leu Met Arg Ser Glu Pro Arg Pro Gly Val Leu
385                 390                 395                 400
Leu Arg Ala Pro Phe Pro
                405
```